(12) United States Patent
McLean

(10) Patent No.: US 11,813,202 B1
(45) Date of Patent: Nov. 14, 2023

(54) CPAP ENCLOSURE

(71) Applicant: Janice McLean, Four Oaks, NC (US)

(72) Inventor: Janice McLean, Four Oaks, NC (US)

( * ) Notice: Subject to any disclaimer, the term of this patent is extended or adjusted under 35 U.S.C. 154(b) by 884 days.

(21) Appl. No.: 16/847,758

(22) Filed: Apr. 14, 2020

(51) Int. Cl.
*A61M 16/00* (2006.01)
*A61G 10/04* (2006.01)
*A61G 10/02* (2006.01)
*A61M 16/08* (2006.01)
*A61M 16/20* (2006.01)

(52) U.S. Cl.
CPC ............. *A61G 10/04* (2013.01); *A61G 10/02* (2013.01); *A61M 16/0063* (2014.02); *A61M 16/0875* (2013.01); *A61M 16/20* (2013.01)

(58) Field of Classification Search
CPC ....................................................... A61G 10/04
See application file for complete search history.

(56) References Cited

U.S. PATENT DOCUMENTS

| | | | | |
|---|---|---|---|---|
| 1,858,400 A * | 5/1932 | Koehler | ........... | A61M 16/00 |
| | | | | 128/204.15 |
| 1,913,347 A * | 6/1933 | Taylor | ........... | A61G 10/04 |
| | | | | 128/204.15 |
| 1,971,408 A * | 8/1934 | Heldbrink | ........... | A61G 10/04 |
| | | | | 128/205.26 |
| 2,190,613 A * | 2/1940 | Sittler | ........... | A61G 10/04 |
| | | | | 128/205.26 |
| 2,191,024 A * | 2/1940 | Matheny | ........... | A61G 10/04 |
| | | | | 135/92 |
| 2,389,293 A * | 11/1945 | Blosser | ........... | A61G 10/04 |
| | | | | 128/205.26 |
| 2,463,090 A * | 3/1949 | Dixon | ........... | F24F 1/022 |
| | | | | 135/96 |
| 2,470,587 A * | 5/1949 | Taylor | ........... | A61G 10/04 |
| | | | | 5/503.1 |
| 2,503,725 A * | 4/1950 | Greene | ........... | A61G 10/04 |
| | | | | 128/205.26 |
| 2,508,050 A * | 5/1950 | Valente | ........... | A61G 10/04 |
| | | | | 128/205.26 |
| 2,603,214 A * | 7/1952 | Taylor | ........... | A61G 10/04 |
| | | | | 135/96 |
| 2,664,890 A * | 1/1954 | Wallace | ........... | A61G 10/04 |
| | | | | 128/205.26 |
| 2,694,403 A * | 11/1954 | Hudson | ........... | A61G 10/04 |
| | | | | 135/117 |

(Continued)

*Primary Examiner* — LaToya M Louis
(74) *Attorney, Agent, or Firm* — Kyle A. Fletcher, Esq.

(57) ABSTRACT

The CPAP enclosure is for use in treating sleep apnea in a patient. The CPAP enclosure creates a protected space that contains atmospheric gases at an increased pressure. The increased pressure created within the protected space of the CPAP enclosure prevents the narrowing of the patient's breathing airways during sleep. The CPAP enclosure includes a tent, a valve structure, and a CPAP machine. The tent forms the protected space of the CPAP enclosure. The CPAP machine generates a flow of atmospheric gas under pressure that is pumped into the protected space of the CPAP enclosure. The valve structure controls the flow of atmospheric gas under pressure from the CPAP machine into the protected space of the CPAP enclosure. The valve structure controls the pressure of the atmospheric gas contained within the protected space of the CPAP enclosure.

18 Claims, 5 Drawing Sheets

(56) References Cited

U.S. PATENT DOCUMENTS

| | | | | |
|---|---|---|---|---|
| 2,699,775 | A * | 1/1955 | Cameto | A61G 10/04 128/205.26 |
| 2,702,546 | A * | 2/1955 | Gilroy | A61G 10/04 135/96 |
| 2,742,040 | A * | 4/1956 | Moore | A61G 10/04 62/304 |
| 2,915,074 | A * | 12/1959 | Cameto | E04H 15/20 52/2.21 |
| 3,000,379 | A * | 9/1961 | Viers | A61G 10/04 128/205.26 |
| 3,006,339 | A | 10/1961 | Smith | |
| 3,050,058 | A * | 8/1962 | Andrews, Jr. | A61G 10/04 417/420 |
| 3,071,134 | A * | 1/1963 | Pate | A61G 10/04 128/201.23 |
| 3,090,382 | A * | 5/1963 | Fegan | A61G 10/04 62/289 |
| 3,272,199 | A * | 9/1966 | Matthews | A61G 10/005 135/117 |
| 3,294,088 | A * | 12/1966 | Boehmer | A61G 10/04 62/3.2 |
| 3,306,289 | A * | 2/1967 | Cameto | A61G 10/02 128/200.14 |
| 3,318,308 | A * | 5/1967 | Grosholz | A61G 10/04 128/204.15 |
| 3,404,684 | A * | 10/1968 | Brewer, Jr. | A61G 10/04 128/204.15 |
| 3,518,991 | A * | 7/1970 | Goss | A61G 10/04 312/3 |
| 3,540,446 | A * | 11/1970 | Dixon | A61G 10/04 128/205.26 |
| 3,552,391 | A * | 1/1971 | Deaton | A61G 10/04 128/205.26 |
| 3,703,173 | A * | 11/1972 | Dixon | A61G 10/04 128/200.14 |
| 3,763,507 | A * | 10/1973 | Propst | A47D 7/00 5/100 |
| 3,786,809 | A * | 1/1974 | Kitrilakis | A61M 16/0627 128/205.26 |
| 3,798,685 | A * | 3/1974 | Hunt | A61G 1/04 5/505.1 |
| 3,859,993 | A * | 1/1975 | Bitner | A61M 16/009 5/507.1 |
| 3,999,541 | A * | 12/1976 | Tabor | A61G 10/04 128/204.15 |
| 4,407,280 | A * | 10/1983 | Trammell | A61M 16/0627 128/205.26 |
| 4,505,190 | A * | 3/1985 | Fink | B08B 15/026 454/56 |
| 5,245,998 | A * | 9/1993 | Sundsrud | A61G 10/04 128/200.24 |
| 5,396,904 | A * | 3/1995 | Hartigan, Jr. | A61B 50/13 128/853 |
| 5,832,919 | A | 11/1998 | Kano | |
| 6,001,057 | A * | 12/1999 | Bongiovanni | A61G 10/04 5/629 |
| 6,062,215 | A | 5/2000 | Leininger | |
| 6,192,633 | B1 * | 2/2001 | Hilbert | E04H 15/20 52/87 |
| 6,367,476 | B1 * | 4/2002 | Conn | A61G 10/04 135/121 |
| 7,037,188 | B2 * | 5/2006 | Schmid | A47C 21/044 55/467 |
| 7,174,584 | B2 * | 2/2007 | Danaher | E04H 15/40 135/96 |
| 7,818,835 | B2 * | 10/2010 | Heaton | A61F 7/02 5/284 |
| 3,025,055 | A1 | 9/2011 | Grady | |
| D681,146 | S | 4/2013 | Sperry | |
| 10,154,934 | B2 | 12/2018 | Canty | |
| 10,548,413 | B2 * | 2/2020 | Smith | A47D 9/005 |
| 10,624,813 | B2 * | 4/2020 | Monterenzi | A61M 35/30 |
| 10,967,204 | B1 * | 4/2021 | Adams | B01D 46/10 |
| 11,439,554 | B2 * | 9/2022 | Breegi | A61G 11/009 |
| 2016/0309916 | A1 * | 10/2016 | Pothen | A61B 5/0077 |

* cited by examiner

CPAP ENCLOSURE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science including personal accommodations especially adapted for patients, more specifically, a treatment enclosure for medical purposes. (A61G10/00)

SUMMARY OF INVENTION

The CPAP enclosure is a therapeutic structure. The CPAP enclosure is configured for use with a patient. The CPAP enclosure is configured for use in treating sleep apnea in a patient. The CPAP enclosure creates a protected space that contains atmospheric gases at an increased pressure. The increased pressure created within the protected space of the CPAP enclosure prevents the narrowing of the patient's breathing airways during sleep. The CPAP enclosure comprises a tent, a valve structure, and a CPAP machine. The tent forms the protected space of the CPAP enclosure. The CPAP machine generates a flow of atmospheric gas under pressure that is pumped into the protected space of the CPAP enclosure. The valve structure controls the flow of atmospheric gas under pressure from the CPAP machine into the protected space of the CPAP enclosure. The valve structure controls the pressure of the atmospheric gas contained within the protected space of the CPAP enclosure.

These together with additional objects, features and advantages of the CPAP enclosure will be readily apparent to those of ordinary skill in the art upon reading the following detailed description of the presently preferred, but nonetheless illustrative, embodiments when taken in conjunction with the accompanying drawings.

In this respect, before explaining the current embodiments of the CPAP enclosure in detail, it is to be understood that the CPAP enclosure is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the CPAP enclosure.

It is therefore important that the claims be regarded as including such equivalent construction insofar as they do not depart from the spirit and scope of the CPAP enclosure. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
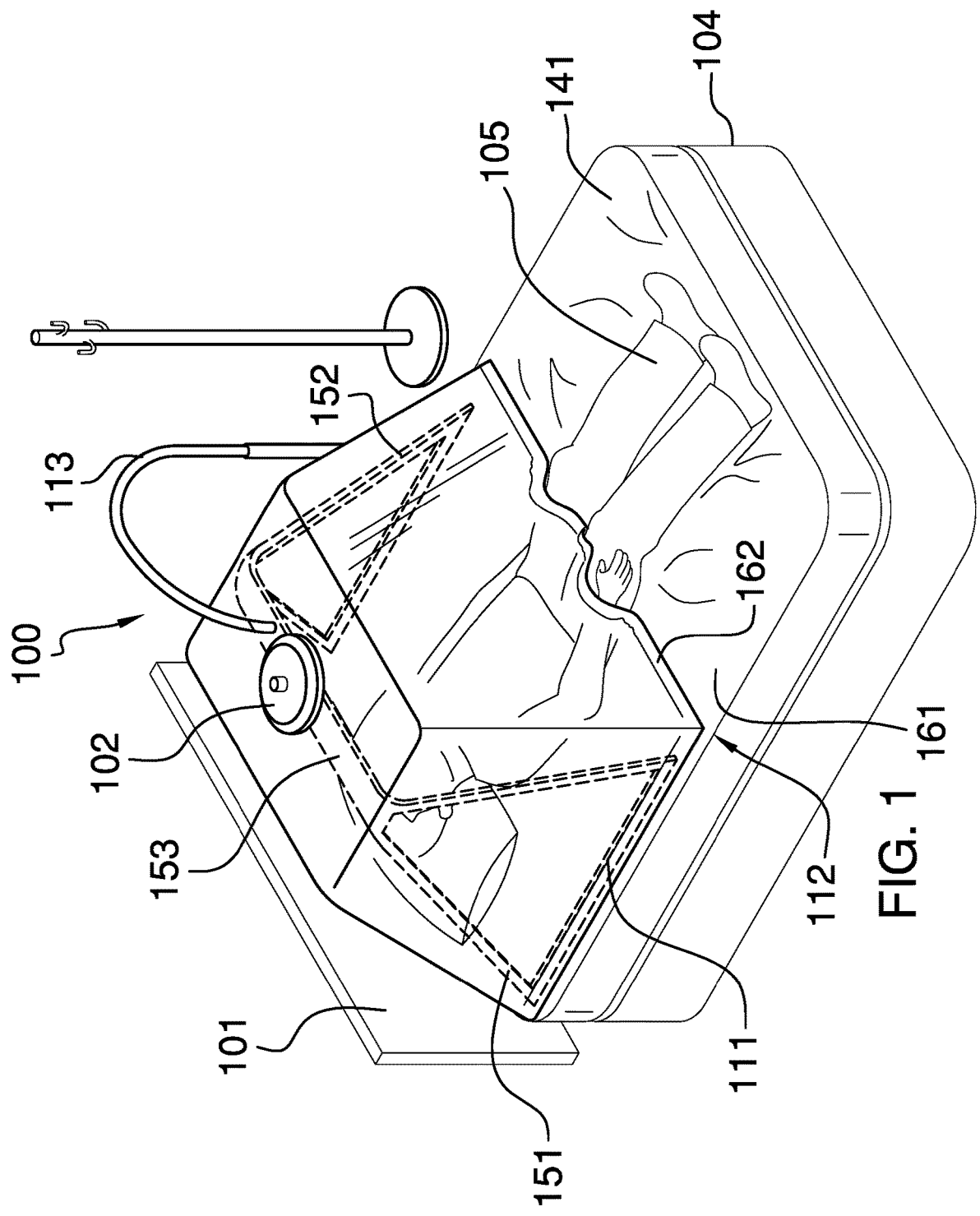
FIG. 1 is an in-use view of an embodiment of the disclosure.
Figure 2:
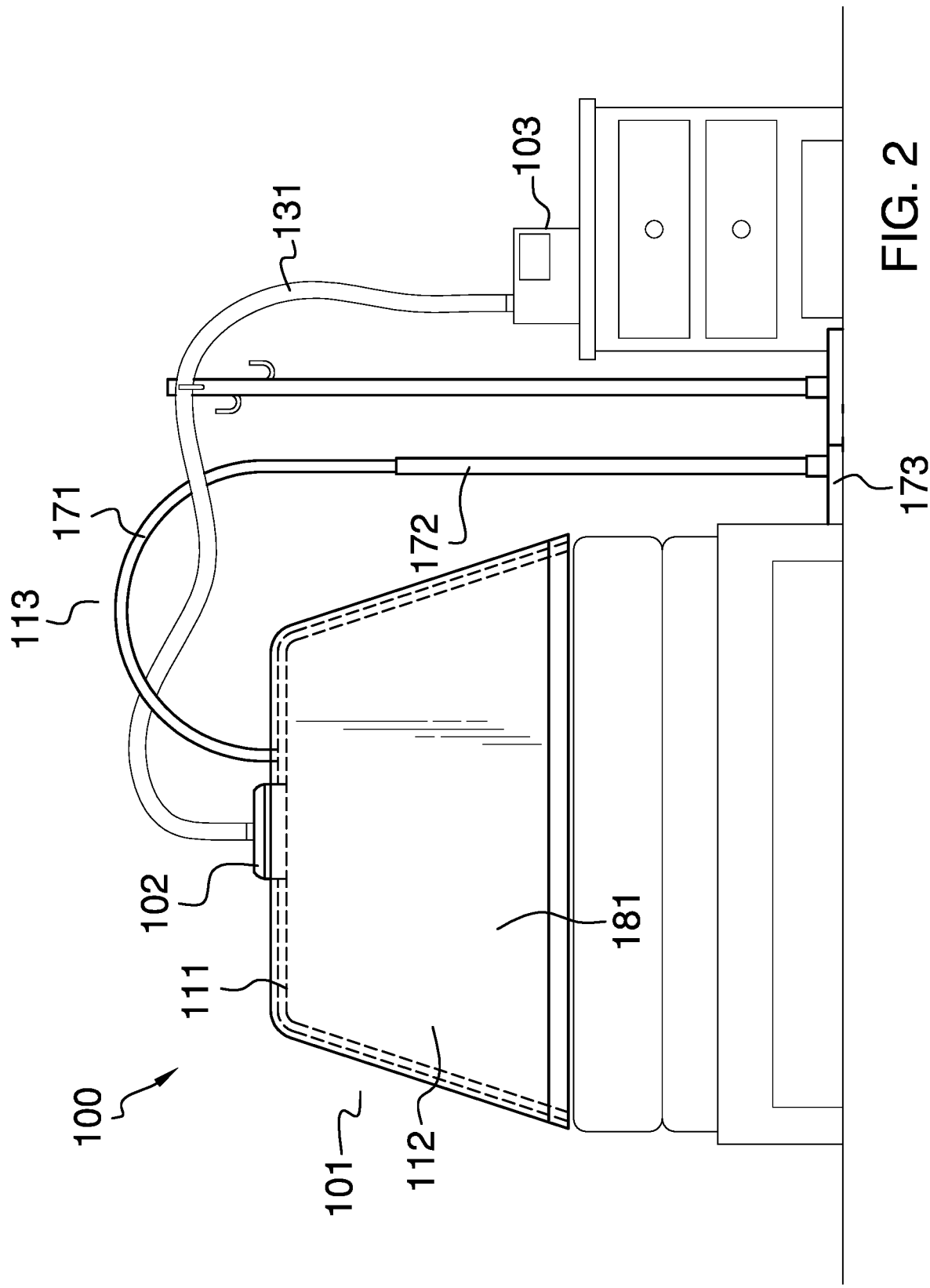
FIG. 2 is a front view of an embodiment of the disclosure.
Figure 3:
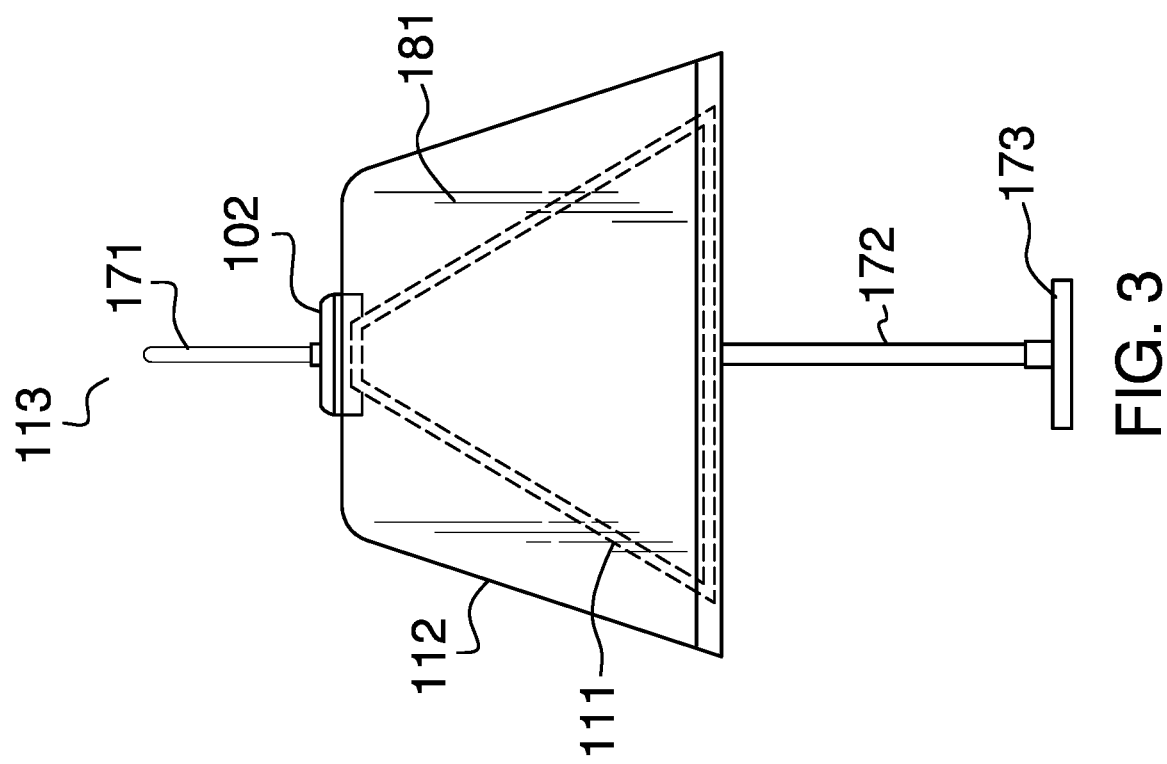
FIG. 3 is a side view of an embodiment of the disclosure.
Figure 4:
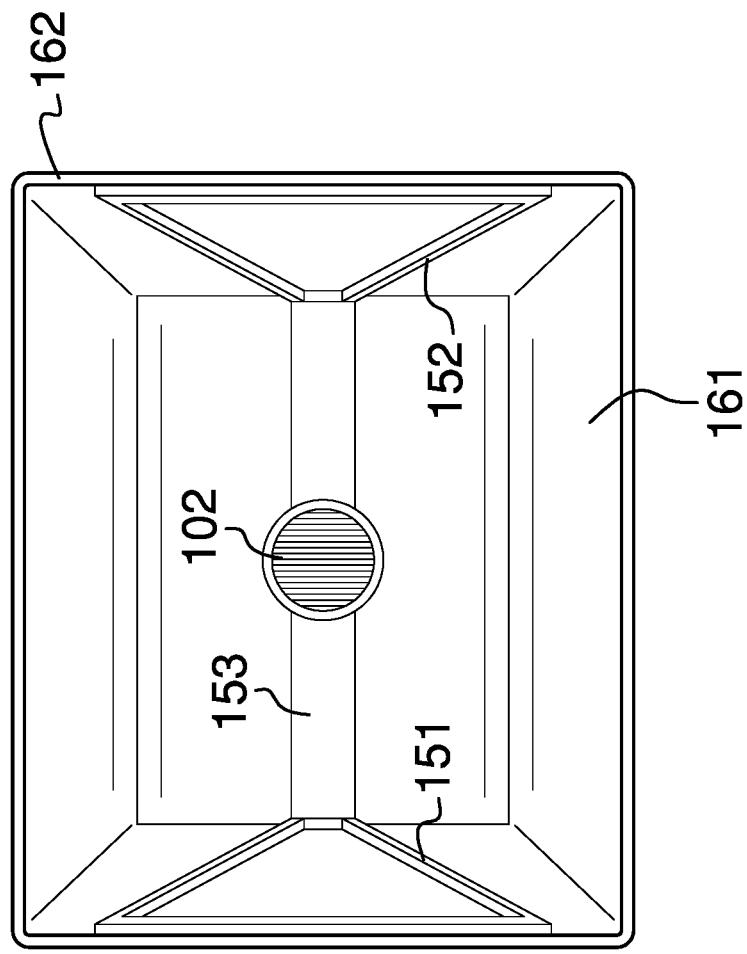
FIG. 4 is a bottom view of an embodiment of the disclosure.
Figure 5:
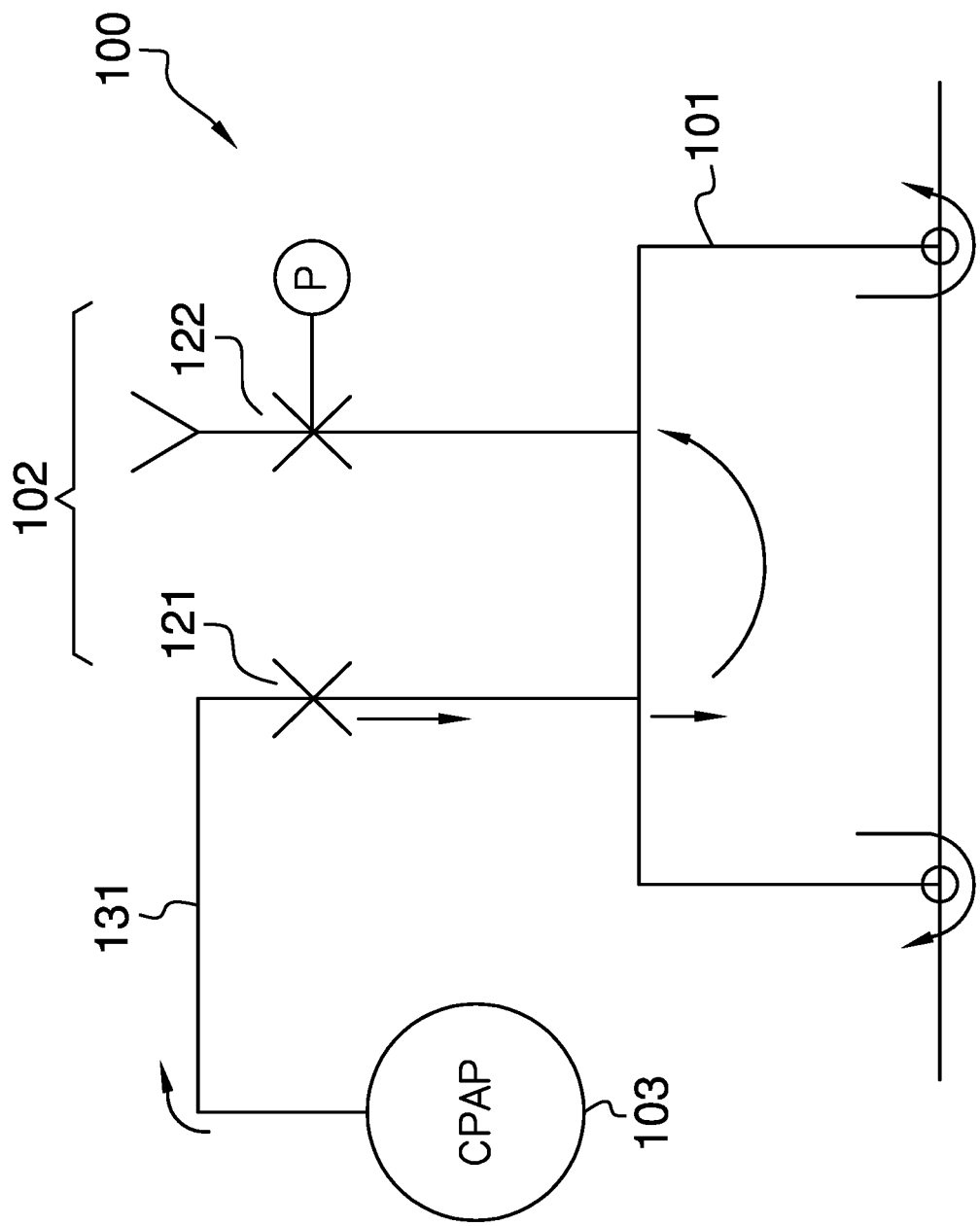
FIG. 5 is a schematic view of an embodiment of the disclosure.

Detailed reference will now be made to one or more potential embodiments of the disclosure, which are illustrated in FIGS. 1 through 5.

The CPAP enclosure 100 (hereinafter invention) is a therapeutic structure. The invention 100 is configured for use with a patient 105. The invention 100 is configured for use in treating sleep apnea in a patient 105. The invention 100 creates a protected space 181 that contains atmospheric gases at an increased pressure. The increased pressure created within the protected space 181 of the invention 100 prevents the narrowing of the patient's 105 breathing airways during sleep. The invention 100 comprises a tent 101, a valve structure 102, and a CPAP machine 103. The tent 101 forms the protected space 181 of the invention 100. The CPAP machine 103 generates a flow of atmospheric gas under pressure that is pumped into the protected space 181 of the invention 100. The valve structure 102 controls the flow of atmospheric gas under pressure from the CPAP machine 103 into the protected space 181 of the invention 100. The valve structure 102 controls the pressure of the atmospheric gas contained within the protected space 181 of the invention 100.

The bed 104 is a cushioned horizontally oriented surface. The patient 105 rests on the superior surface 141 of the bed 104 while receiving therapeutic benefits from the invention 100. The superior surface 141 forms the horizontally oriented supporting surface of the bed 104. The patient 105 is an individual designated to receive the therapeutic benefits from the invention 100. The patient 105 is defined elsewhere in this disclosure.

The CPAP machine 103 is a mechanical device. The CPAP machine 103 is a medical device. The CPAP machine 103 is a therapeutic device. The CPAP machine 103 compresses atmospheric gas that is used therapeutically by the patient 105. The CPAP machine 103 transports the compressed atmospheric gas into the protected space 181 of the tent 101. The increased pressure of the atmospheric gas generated by the CPAP machine 103 in the protected space 181 of the tent 101 relieves the symptoms of sleep apnea in the patient 105. The CPAP machine 103 further comprises a CPAP hose 131.

The CPAP hose 131 is a hose. The hose is a fluid transport structure. The hose is defined elsewhere in this disclosure. The CPAP hose 131 forms a fluidic connection between the CPAP intake valve 121 of the valve structure 102 and the CPAP machine 103. The CPAP hose 131 transports the compressed atmospheric gas from the CPAP machine 103 to the CPAP intake valve 121.

The tent 101 is a mechanical structure. The tent 101 is a portable structure. The tent 101 creates a protected space 181 that encloses the patient 105. While the protected space 181 of the tent 101 is not completely gas impermeable, the exterior surfaces of the tent 101 are formed from a gas impermeable sheeting that allows the CPAP machine 103 to generate an atmospheric gas pressure differential between the interior and exterior surfaces of the tent 101. The atmospheric gas pressure generated within the interior of the protected space 181 of the tent 101 by the CPAP machine 103 creates a therapeutic effect for the patient 105 that inhibits the occurrence of sleep apnea in the patient 105. The tent 101 comprises a framework 111, a shell 112, a jib 171 structure 113, and a protected space 181.

The framework 111 is a mechanical structure. The framework 111 is formed as a u-shaped structure. The framework 111 forms a load path that suspends the shell 112 above the patient 105. The load path formed by the framework 111 transfers the load of the shell 112 to the superior surface 141 of the bed 104. The load path formed by the framework 111 alternately transfers the load of the shell 112 to the jib 171 structure 113 of the tent 101. The framework 111 forms a skeleton that holds the shell 112 in the form factor of the protected space 181 of the tent 101 during the use of the invention 100. The framework 111 comprises a first wing 151, a second wing 152, and a crossbeam 153.

The crossbeam 153 is a prism-shaped structure. The crossbeam 153 forms the crossbeam 153 of the u-shaped structure that forms the framework 111. The crossbeam 153 attaches the first wing 151 to the second wing 152. The jib 171 structure 113 attaches to the crossbeam 153 to suspend the tent 101 above the bed 104.

The first wing 151 is a prism-shaped structure. The first wing 151 is a disk-shaped structure. The first wing 151 has a triangular shape. The first wing 151 forms the first arm of the u-shaped structure that forms the framework 111. The first wing 151 projects away from the crossbeam 153 in the inferior direction. The first wing 151 forms a portion of the load path that transfers the load of the tent 101 to the superior surface 141 of the bed 104 when the first wing 151 rests on the bed 104.

The second wing 152 is a prism-shaped structure. The second wing 152 is a disk-shaped structure. The second wing 152 has a triangular shape. The second wing 152 forms the second arm of the u-shaped structure that forms the framework 111. The second wing 152 attaches to the congruent end of the prism structure of the crossbeam 153 that is distal from the first wing 151. The second wing 152 projects away from the crossbeam 153 in the inferior direction. The second wing 152 forms a portion of the load path that transfers the load of the tent 101 to the superior surface 141 of the bed 104 when the second wing 152 rests on the bed 104.

The shell 112 is a plastic structure. The shell 112 is a sheeting structure. The shell 112 forms a gas impermeable surface that encloses the protected space 181 of the tent 101. The shell 112 drapes over the skeleton formed by the framework 111 to form the protected space 181 of the tent 101. The shell 112 comprises a sheeting 161 and a weighted hem 162.

The sheeting 161 is a plastic sheeting. The sheeting 161 is a flexible sheeting structure. The sheeting 161 is a gas impermeable structure. The sheeting 161 drapes over the skeleton formed by the framework 111 to create the protected space 181 of the tent 101. The sheeting 161 forms exterior surfaces of the protected space 181 of the tent 101. The weighted hem 162 is a hem that is formed around the perimeter edges of the sheeting 161. The weighted hem 162 is a weighted structure such that the weight of the weighted hem 162 inhibits the pressurized atmospheric gases contained within the protected space 181 from lifting the weighted hem 162 above the superior surface 141 of the bed 104.

The jib 171 structure 113 is a mechanical structure. The jib 171 structure 113 forms a load path that suspends the tent 101 above the superior surface 141 of the bed 104. The jib 171 structure 113 comprises a jib 171, a stanchion 172, and a pedestal 173.

The pedestal 173 is a prism-shaped structure. The pedestal 173 is a disk-shaped structure. The pedestal 173 forms the final link in the load path that transfers a portion of the load of the tent 101 and the full loads of the stanchion 172 and the pedestal 173 to a supporting surface. The stanchion 172 is a prism-shaped structure.

The stanchion 172 is a vertically oriented structure. The stanchion 172 is an extension structure. The stanchion 172 attaches the jib 171 to the pedestal 173. The stanchion 172 sets the reach between the jib 171 and the pedestal 173 such that the jib 171 suspends the load of the tent 101 above the superior surface 141 of the bed 104.

The jib 171 is a prism-shaped structure. In the first potential embodiment of the disclosure, the jib 171 is a non-Euclidean structure. The jib 171 attaches to the end of the stanchion 172 that is distal from the pedestal 173. The jib 171 attaches to the stanchion 172 in the manner of a cantilever. The jib 171 projects away from the stanchion 172 such that the jib 171 overhangs the superior surface 141 of the bed 104. The free end of the jib 171 suspends the crossbeam 153 of the framework 111 above the superior surface 141 of the bed 104.

The term protected space 181 is defined elsewhere in this disclosure.

The valve structure 102 controls a portion of the flow of atmospheric gases into and out of the protected space 181 of the tent 101. The valve structure 102 controls the atmospheric gas flow in a direction selected from the group consisting of: a) atmospheric gas flowing under pressure from the CPAP machine 103 into the protected space 181 of the tent 101; and, b) atmospheric gas flowing from the protected space 181 of the tent 101 into the atmospheric gas surrounding the exterior surfaces of the tent 101. The valve structure 102 attaches to the shell 112 of the tent 101. The valve structure 102 comprises a CPAP intake valve 121 and a pressure relief valve 122.

The CPAP intake valve 121 is a valve that forms a fluidic connection between the CPAP machine 103 and the protected space 181 of the tent 101. The CPAP intake valve 121 opens and closes to control the flow of pressurized atmospheric gas between the CPAP machine 103 and the protected space 181 of the tent 101. The CPAP intake valve 121 receives atmospheric gas under pressure from the CPAP machine 103 and transfers the received pressurized atmospheric gas into the protected space 181 of the tent 101. The CPAP intake valve 121 physically connects to the CPAP hose 131 of the CPAP machine 103.

The pressure relief valve 122 is a type of pressure valve. The pressure relief valve 122 is defined elsewhere in this disclosure. The pressure relief valve 122 releases atmospheric gas from the interior space of the protected space 181 of the tent 101 into the exterior space surrounding the protected space 181 when the pressure of the atmospheric gas contained in the protected space 181 exceeds a previously determined pressure. The pressure relief valve 122 limits the pressure of the atmospheric gas that can build up in the protected space 181 of the tent 101. The previously determined pressure limit for the atmospheric gas contained in the protected space 181 of the tent 101 that is set into the pressure relief valve 122 is determined by the therapeutic needs of the patient 105 on a case by case basis.

The following definitions were used in this disclosure:

Atmosphere: As used in this disclosure, the atmosphere refers to a blanket of gases (primarily nitrogen and oxygen) that surround the earth. Typical atmospheric conditions are approximated and characterized as the normal temperature and pressure. Atmospheric gases are commonly called air.

Cantilever: As used in this disclosure, a cantilever is a beam or other structure that projects away from an object and is supported on only one end. A cantilever is further defined with a fixed end and a free end. The fixed end is the end of the cantilever that is attached to the object. The free end is the end of the cantilever that is distal from the fixed end.

CPAP: As used in this disclosure, CPAP stands for Continuous Positive Airflow Pressure. CPAP is used as a treatment for obstructive sleep apnea. The continuous positive air flow from a CPAP machine will generate a mild pressure that prevents the patient's airways from collapsing during sleep.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Drape: As used in this disclosure, to drape means to hang a sheeting over at least two sides of a vertically oriented object to form flowing lines and folds.

Elevation: As used in this disclosure, elevation refers to the span of the distance in the superior direction between a specified horizontal surface and a reference horizontal surface. Unless the context of the disclosure suggest otherwise, the specified horizontal surface is the supporting surface the potential embodiment of the disclosure rests on. The infinitive form of elevation is to elevate.

Extension Structure: As used in this disclosure, an extension structure is an inert physical structure that is used to extend or bridge the reach between any two objects.

Exterior: As used in this disclosure, the exterior is used as a relational term that implies that an object is not contained within the boundary of a structure or a space.

Fitting: As used in this disclosure, a fitting is a component that is attached to a first object. The fitting is used to forming a fluidic connection between the first object and a second object.

Fluid: As used in this disclosure, a fluid refers to a state of matter wherein the matter is capable of flow and takes the shape of a container it is placed within. The term fluid commonly refers to a liquid or a gas.

Fluidic Connection: As used in this disclosure, a fluidic connection refers to a tubular structure that transports a fluid from a first object to a second object. Methods to design and use a fluidic connections are well-known and documented in the mechanical, chemical, and plumbing arts.

Fold: As used in this disclosure, to fold means to bend an object back upon itself.

Force of Gravity: As used in this disclosure, the force of gravity refers to a vector that indicates the direction of the pull of gravity on an object at or near the surface of the earth.

Framework: As used in this disclosure, a framework refers to the substructure of an object that carries the load path of the object.

Gas: As used in this disclosure, a gas refers to a state (phase) of matter that is fluid and that fills the volume of the structure that contains it. Stated differently, the volume of a gas always equals the volume of its container.

Hem: As used in this disclosure, a hem is a treatment applied to the edge of a textile wherein the edge is folded over onto the textile and attached with a seam to the textile. A weighted hem is a hem that is formed with weights such that the mass of the hem holds the hem is a position.

Horizontal: As used in this disclosure, horizontal is a directional term that refers to a direction that is either: 1) parallel to the horizon; 2) perpendicular to the local force of gravity, or, 3) parallel to a supporting surface. In cases where the appropriate definition or definitions are not obvious, the second option should be used in interpreting the specification. Unless specifically noted in this disclosure, the horizontal direction is always perpendicular to the vertical direction.

Hose: As used in this disclosure, a hose is a flexible hollow prism-shaped device that is used for transporting liquids and gases. When referring to a hose in this disclosure, the terms inner dimension and outer dimension are used as they would be used by those skilled in the plumbing arts.

Inferior: As used in this disclosure, the term inferior refers to a directional reference that is parallel to and in the same direction as the force of gravity when an object is positioned or used normally.

Interior: As used in this disclosure, the interior is used as a relational term that implies that an object is contained within the boundary of a structure or a space.

Jib: As used in this disclosure, a jib is a beam structure that: 1) is mounted with a free end in the manner of a cantilever; and, 2) suspends a load at the free end of the jib. In multicomponent beam structures, such as with a crane, the jib is the sub-structure that physically suspends the load.

Liquid: As used in this disclosure, a liquid refers to a state (phase) of matter that is fluid and that maintains, for a given pressure, a fixed volume that is independent of the volume of the container.

Load: As used in this disclosure, the term load refers to an object upon which a force is acting or which is otherwise absorbing energy in some fashion. Examples of a load in this sense include, but are not limited to, a mass that is being moved a distance or an electrical circuit element that draws energy. The term load is also commonly used to refer to the forces that are applied to a stationary structure.

Load Path: As used in this disclosure, a load path refers to a chain of one or more structures that transfers a load generated by a raised structure or object to a foundation, supporting surface, or the earth.

Non-Euclidean Prism: As used in this disclosure, a non-Euclidean prism is a prism structure wherein the center axis of the prism lies on a non-Euclidean plane or is otherwise formed with a curvature.

Not Significantly Different: As used in this disclosure, the term not significantly different compares a specified property of a first object to the corresponding property of a reference object (reference property). The specified property is considered to be not significantly different from the reference property when the absolute value of the difference between the specified property and the reference property is less than 10.0% of the reference property value. A negligible difference is considered to be not significantly different.

Patient: As used in this disclosure, a patient is a person who is designated to receive a medical treatment, therapy or service. The term patient may be extended to an animal when used within the context of the animal receiving veterinary treatment or services.

Pedestal: As used in this disclosure, a pedestal is an intermediary load bearing structure that that forms a load path between a supporting surface and an object, structure, or load.

Pressure: As used in this disclosure, pressure refers to a measure of force per unit area.

Pressure Valve: As used in this disclosure, a pressure valve is a valve selected from a class of valves configured to control the pressure of a fluid contained within a contained structure or space. A pressure relief valve is a valve that opens to release the fluid contained in contained structure or space when the pressure within the contained structure or space is greater than a predetermined pressure. A constant pressure valve maintains a constant pressure within the contained structure or space. The constant pressure valve controls the flow of fluid from a pressurized fluid source when the pressure of the fluid contained in the contained structure or space falls below a previously determined temperature. A fixed pressure drop valve controls the flow of fluid from a pressurized fluid source to maintain a constant pressure differential between the fluid provided by the pressurized fluid source and the fluid contained in the contained structure or space.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Protected Space: As used in this disclosure, a protected space is a space formed by a boundary structure. The boundary structure forms a barrier that protects objects within the protected space from potential dangers from the other side of the boundary.

Pump: As used in this disclosure, a pump is a mechanical device that uses suction or pressure to raise or move fluids, compress fluids, or force a fluid into an inflatable object. Within this disclosure, a compressor refers to a pump that is dedicated to compressing a fluid or placing a fluid under pressure.

Quick Connect Fitting: As used in this disclosure, a quick connect fitting is a coupling that is used in fluid flow applications to quickly connect or disconnect two lines or two objects through which fluids will flow. Connections or disconnections are intended to be done by hand without the use of tools. Quick connect fittings readily and commercially available and methods for their selection and use well known and documented in the mechanical, chemical, and plumbing arts.

Reach: As used in this disclosure, reach refers to a span of distance between any two objects.

Roughly: As used in this disclosure, roughly refers to a comparison between two objects. Roughly means that the difference between one or more parameters of the two compared objects are not significantly different.

Seam: As used in this disclosure, a seam is a joining of: 1) a first textile to a second textile; 2) a first sheeting to a second sheeting; or, 3) a first textile to a first sheeting. Potential methods to form seams include, but are not limited to, a sewn seam, a heat bonded seam, an ultrasonically bonded seam, a laser seam, or a seam formed using an adhesive.

Sewn Seam: As used in this disclosure, a sewn seam a method of attaching two or more layers of textile, leather, or other material through the use of a thread, a yarn, or a cord that is repeatedly inserted and looped through the two or more layers of textile, leather, or other material.

Sheeting: As used in this disclosure, a sheeting is a material, such as a paper, textile, a plastic, or a metal foil, in the form of a thin flexible layer or layers. The sheeting forms a disk structure. The two surfaces of the sheeting with the greatest surface area are called the faces of the sheeting.

Skeleton: As used in this disclosure, a skeleton is a framework that supports a sheeting such that the sheeting maintains a roughly fixed form factor.

Stanchion: As used in this disclosure, a stanchion refers to a vertically oriented prism-shaped pole, post, or support.

Superior: As used in this disclosure, the term superior refers to a directional reference that is parallel to and in the opposite direction of the force of gravity when an object is positioned or used normally.

Supporting Surface: As used in this disclosure, a supporting surface is a horizontal surface upon which an object is placed and to which the load path of the object is transferred. This disclosure assumes that an object placed on the supporting surface is in an orientation that is appropriate for the normal or anticipated use of the object.

Suspend: As used in this disclosure, to suspend an object means to support an object such that the inferior end of the object does not form a significant portion of the load path of the object. Include inferior superior and load path.

Tent: As used in this disclosure, a tent is a portable structure used to form a protected space. The tent typically comprises a sheeting that forms the exterior surfaces of the tent and a framework that supports the sheeting to create a protected space.

Therapeutic: As used in this disclosure, therapeutic is an adjective that refers to a medical, ameliorative, or hygienic substance, process, or procedure.

U-Shaped Structure: As used in this disclosure, a U-shaped structure refers to a three-sided structure comprising a crossbeam, a first arm, and a second arm. In a U-shaped structure, the first arm and the second arm project away from the crossbeam: 1) in the same direction; 2) at roughly equivalent angles to the crossbeam, and, 3) the span of the length of the first arm roughly equals the span of the length of the second arm. The first arm and the second arm project away from the crossbeam in the manner of a cantilever.

Valve: As used in this disclosure, a valve is a device that is used to control the flow of a fluid (gas or liquid) through a pipe, tube, or hose.

Vertical: As used in this disclosure, vertical refers to a direction that is either: 1) perpendicular to the horizontal direction; 2) parallel to the local force of gravity; or, 3) when referring to an individual object the direction from the designated top of the individual object to the designated bottom of the individual object. In cases where the appropriate definition or definitions are not obvious, the second option should be used in interpreting the specification. Unless specifically noted in this disclosure, the vertical direction is always perpendicular to the horizontal direction.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A therapeutic device comprising a tent, a valve structure, and a CPAP machine; wherein the therapeutic device is configured for use with a patient; wherein the therapeutic device is configured for use with a bed; wherein the therapeutic device is configured for use in treating sleep apnea in a patient; wherein the therapeutic device creates a protected space; wherein the tent forms the protected space of the therapeutic device; wherein the CPAP machine generates a flow of atmospheric gas under pressure;

wherein the tent comprises a framework, a shell, and a jib structure; wherein the framework comprises a first wing, a second wing, and a crossbeam; wherein the crossbeam is a prism-shaped structure; wherein the crossbeam forms a u-shaped structure that forms the framework; wherein the crossbeam attaches the first wing to the second wing; wherein the jib structure attaches to the crossbeam to suspend the tent above the bed; wherein the first wing has a triangular shape; wherein the first wing forms the first arm of the u-shaped structure that forms the framework;

wherein the first wing projects away from the crossbeam in an inferior direction;

wherein the first wing forms a portion of a load path that transfers the load of the tent to a superior surface of the bed when the first wing rests on the bed;

wherein the second wing has a triangular shape;

wherein the second wing forms the second arm of the u-shaped structure that forms the framework;

wherein the second wing attaches to a congruent end of the prism structure of the crossbeam that is distal from the first wing;

wherein the second wing projects away from the crossbeam in the inferior direction;

wherein the second wing forms a portion of the load path that transfers the load of the tent to the superior surface of the bed when the second wing rests on the bed.

2. The therapeutic device according to claim 1 wherein the valve structure controls the flow of atmospheric gas under pressure from the CPAP machine into the protected space of the therapeutic device;

wherein the valve structure controls the pressure of the atmospheric gas contained within the protected space of the therapeutic device;

wherein a superior surface forms a horizontally oriented supporting surface of the bed;

wherein the protected space that contains atmospheric gases are at an increased pressure;

wherein the flow of atmospheric gas under pressure is pumped into the protected space of the therapeutic device.

3. The therapeutic device according to claim 2 wherein the CPAP machine is a mechanical device;

wherein the CPAP machine is a medical device;

wherein the CPAP machine is a therapeutic device;

wherein the CPAP machine compresses atmospheric gas that is used therapeutically by the patient;

wherein the CPAP machine transports the compressed atmospheric gas into the protected space.

4. The therapeutic device according to claim 3 wherein the CPAP machine further comprises a CPAP hose;

wherein the CPAP hose is a hose;

wherein the hose is a fluid transport structure.

5. The therapeutic device according to claim 4 wherein the CPAP hose forms a fluidic connection between the valve structure and the CPAP machine.

6. The therapeutic device according to claim 5 wherein the tent is a mechanical structure;

wherein the tent is a portable structure;

wherein the tent creates the protected space that encloses the patient.

7. The therapeutic device according to claim 6 wherein the exterior surfaces of the tent are gas impermeable structures.

8. The therapeutic device according to claim 7 wherein the valve structure controls a portion of the flow of atmospheric gases into and out of the protected space of the tent;

wherein the valve structure controls the atmospheric gas flow in a direction selected from the group consisting of: a) atmospheric gas flowing under pressure from the CPAP machine into the protected space of the tent; and, b) atmospheric gas flowing from the protected space of the tent into the atmospheric gas surrounding the exterior surfaces of the tent;

wherein the valve structure attaches to the tent.

9. The therapeutic device according to claim 8, wherein the framework forms the load path that suspends the shell above the patient wherein the load path formed by the framework transfers the load of the shell to the superior surface of the bed;

wherein the load path formed by the framework alternately transfers the load of the shell to the jib structure of the tent; wherein the jib structure is a mechanical structure; wherein the jib structure forms a load path that suspends the tent above the superior surface of the bed.

10. The therapeutic device according to claim 9
wherein the valve structure comprises a CPAP intake valve and a pressure relief valve;
wherein the CPAP intake valve is a valve that forms a fluidic connection between the CPAP machine and the protected space of the tent;
wherein the pressure relief valve releases atmospheric gas from the interior space of the protected space of the tent into the exterior space surrounding the protected space when the pressure of the atmospheric gas contained in the protected space exceeds a previously determined pressure.

11. The therapeutic device according to claim 9
wherein the framework is a mechanical structure;
wherein the framework is formed as a u-shaped structure;
wherein the framework forms a skeleton that holds the shell in the form factor of the protected space of the tent during the use of the therapeutic device.

12. The therapeutic device according to claim 11
wherein the shell is a plastic structure;
wherein the shell is a sheeting structure;
wherein the shell forms a gas impermeable surface that encloses the protected space of the tent;
wherein the shell drapes over the skeleton formed by the framework to form the protected space of the tent.

13. The therapeutic device according to claim 12
wherein the shell comprises a sheeting and a weighted hem;
wherein the weighted hem is a hem that is formed around the perimeter edges of the sheeting.

14. The therapeutic device according to claim 13
wherein the sheeting is a plastic sheeting;
wherein the sheeting is a flexible sheeting structure;
wherein the sheeting is a gas impermeable structure;
wherein the sheeting drapes over the skeleton formed by the framework to create the protected space of the tent;
wherein the sheeting forms exterior surfaces of the protected space of the tent.

15. The therapeutic device according to claim 14 wherein the weighted hem is a weighted structure such that the weight of the weighted hem inhibits the pressurized atmospheric gases contained within the protected space from lifting the weighted hem above the superior surface of the bed.

16. The therapeutic device according to claim 15, wherein the jib structure comprises a jib, a stanchion, and a pedestal;
wherein the pedestal is a prism-shaped structure;
wherein the pedestal forms a final link in the load path that transfers a portion of the load of the tent and full loads of the stanchion and the pedestal to a supporting surface;
wherein the stanchion is a prism-shaped structure;
wherein the stanchion is a vertically oriented structure;
wherein the stanchion is an extension structure;
wherein the stanchion attaches the jib to the pedestal;
wherein the stanchion sets a reach between the jib and the pedestal such that the jib suspends the load of the tent above the superior surface of the bed;
wherein the jib is a prism-shaped structure;
wherein the jib is a non-Euclidean structure;
wherein the jib attaches to the end of the stanchion that is distal from the pedestal;
wherein the jib attaches to the stanchion to form a cantilever;
wherein the jib projects away from the stanchion such that the jib overhangs the superior surface of the bed;
wherein the free end of the jib suspends the crossbeam of the framework above the superior surface of the bed.

17. The therapeutic device according to claim 16
wherein the CPAP intake valve opens and closes to control the flow of pressurized atmospheric gas between the CPAP machine and the protected space of the tent;
wherein the CPAP intake valve receives atmospheric gas under pressure from the CPAP machine and transfers the received pressurized atmospheric gas into the protected space of the tent;
wherein the CPAP intake valve physically connects to the CPAP hose of the CPAP machine;
wherein the CPAP hose transports the compressed atmospheric gas from the CPAP machine to the CPAP intake valve.

18. The therapeutic device according to claim 17
wherein the pressure relief valve is a pressure valve;
wherein the pressure relief valve limits the pressure of the atmospheric gas that can build up in the protected space of the tent.

* * * * *